United States Patent [19]

Sumimoto et al.

[11] 4,014,876
[45] Mar. 29, 1977

[54] ISOXAZOLE DERIVATIVES

[75] Inventors: Shinzaburo Sumimoto, Osaka; Yoshihiro Tochino, Habikino; Manabu Fujimoto, Nagaokakyo, all of Japan

[73] Assignee: Shionogi & Co., Ltd., Osaka, Japan

[22] Filed: Jan. 19, 1973

[21] Appl. No.: 325,115

Related U.S. Application Data

[63] Continuation-in-part of Ser. No. 88,987, Nov. 12, 1970, abandoned.

[30] Foreign Application Priority Data

Nov. 12, 1969 Japan ............... 44-90619

[52] U.S. Cl. .............. 260/247.2 A; 260/247.1 H; 260/307 H; 424/272; 424/248.54; 424/248.5

[51] Int. Cl.² .............. C07D 295/00; C07D 261/06

[58] Field of Search ............... 260/247.2 A, 307 H

[56] References Cited

FOREIGN PATENTS OR APPLICATIONS 2,164,843   7/1972   Germany .............. 260/247.2

*Primary Examiner*—Paul J. Killos
*Attorney, Agent, or Firm*—Wenderoth, Lind & Ponack

[57] ABSTRACT

Isoxazole derivatives represented by the formula:

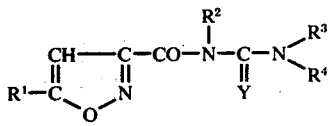

are prepared; wherein $R^1$ and $R^2$ each is hydrogen atom, alkyl group of 1 to 8 carbon atoms, or cycloalkyl group of 3 to 10 carbon atoms; $R^3$ and $R^4$ each is hydrogen atom, alkyl group of 1 to 8 carbon atoms, cycloalkyl group of 3 to 10 carbon atoms, or phenyl group; or the group

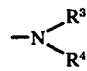

is morpholino group; and Y is oxo group, thioxo group or imino group; being useful as a hypoglycemic and/or a blood free-fatty-acid normalizing antidiabetic agent.

34 Claims, No Drawings

ISOXAZOLE DERIVATIVES

This application is a continuation-in-part of Ser. No. 88,987, filed Nov. 12, 1970, now abandoned.

The present invention relates to isoxazole derivatives, and the production thereof. More particularly, this invention relates to isoxazole derivatives useful as hypoglycemic agents, and the production thereof.

The said isoxazole derivatives are represented by the formula:

$$\underset{R^1-C\diagdown_O\diagup N}{\overset{CH\text{———}C}{\|\quad\|}}-CO-\underset{\underset{Y}{\|}}{N}-\underset{R^4}{\overset{R^2}{|}}\underset{R^4}{\overset{R^3}{\diagup}}\qquad (I)$$

wherein $R^1$ and $R^2$ each is a hydrogen atom, alkyl group of 1 to 8 carbon atoms (e.g. methyl, ethyl, i-propyl, t-butyl, n-amyl, n-octyl), or cycloalkyl group of 3 to 10 carbon atoms (e.g. cyclopropyl, cyclohexyl, adamantyl); $R^3$ and $R^4$ each is a hydrogen atom, alkyl group of 1 to 8 carbon atoms (e.g. methyl, ethyl, i-propyl, t-butyl, n-amyl, n-octyl), cycloalkyl group of 3 to 10 carbon atoms (e.g. cyclopropyl, cyclohexyl, adamantyl), or phenyl group; or the group $$-N\diagup^{R^3}_{\diagdown R^4}$$

is a morpholino group; Y is an oxo group, thioxo group, or imino group.

It is the first object of the present invention to embody the isoxazole derivatives (I). The second object of this invention is to embody the isoxazole derivatives (I) available as hypoglycemic and/or blood free-fatty-acid normalizing agents. The third object of the invention is to embody processes for preparing the isoxazole derivatives (I). These and other objects will be apparent to those conversant with the art to which the present invention pertains, from the subsequent description.

The said isoxazole derivatives (I) can be prepared by reacting a reactive form of isoxazole-3-carboxylic acid (II) with a substituted or unsubstituted area derivative (III). The said reactive form of carboxylic acid (II) is any derivative of an isoxazole-3-carboxylic acid able to give a ureide, thioureide, or guanide, and includes the corresponding acid halogenide, ester, or acid anhydride. The urea derivative (III) includes urea, thiourea, guanidine, and their homologs having at least one hydrogen atom on their nitrogens.

The process of this invention can be shown by the following reaction scheme:

$$\underset{R^1-C\diagdown_O\diagup N}{\overset{CH\text{———}C\text{——}COX}{\|\quad\|}}\ +\ \underset{\underset{Y}{\|}}{H-N}-\underset{R^4}{\overset{R^2}{|}}\underset{R^4}{\overset{R^3}{\diagup}}\ \longrightarrow I$$

$$(II)\qquad\qquad\qquad (III)$$

wherein X is an anion residue of the carboxylic acid selected from the group consisting of a halogen atom (e.g. chlorine, bromine, iodine), lower alkoxy group (e.g. methoxy, ethoxy, t-butoxy), aryloxy group (e.g. p-nitrophenoxy, p-chlorophenoxy), and acyloxy group (e.g. acetoxy, benzoyloxy, p-nitrobenzoyloxy); and $R^1$, $R^2$, $R^3$, $R^4$, and Y have the meanings as defined above.

The starting reactive form of isoxazole-3-carboxylic acids (II) could be prepared, for instance, by 1,3-dipolar cycloaddition of a vinyl alkyl ether or a vinyl acylate to an alkyl chloroximinoacetate in the presence of a tertiary amine with removal of an alkanol or an acid, respectively, or by condensation of a 2,4-diketoaliphatic acid ester with hydroxylamine under ring-closure conditions; followed by transformation of the product into the expected reaction form (II). Examples of the original isoxazole-3-carboxylic acids for the reactive form (II) are as follows:

isoxazole-3-carboxylic acid,
5-methylisoxazole-3-carboxylic acid,
5-ethylisoxazole-3-carboxylic acid,
5-n-propylisoxazole-3-carboxylic acid,
5-i-propylisoxazole-3-carboxylic acid,
5-n-butylisoxazole-3-carboxylic acid,
5-s-butylisoxazole-3-carboxylic acid,
5-n-hexylisoxazole-3-carboxylic acid,
5-n-octylisoxazole-3-carboxylic acid,
5-cyclopropylisoxazole-3-carboxylic acid,
5-cyclohexylisoxazole-3-carboxylic acid, and
5-(1-adamantyl)isoxazole-3-carboxylic acid.

The said urea deriviative (III) includes urea, thiourea, guanidine, and their mono-, di-, or tri-substituted homologs, and can be designated, for example, as follows:

urea,
thiourea,
guanidine,
N-methylurea,
N-ethylurea,
N-n-propylurea,
N-i-propylurea,
N-n-butylurea,
N-s-butylurea,
N-cyclohexylurea,
N-(1-adamantyl)urea,
N-benzylurea,
N-phenylurea,
N,N-dimethylurea,
N,N-diethylurea,
N-methyl-N-ethylurea,
N-n-propyl-N-i-propylurea,
4-morpholinocarbonamide,
N,N'-dimethylurea,
N,N'-diethylurea,
N-methyl-N'-ethylurea,
N,N'-di-i-propylurea,
N,N'-dicyclohexylurea,
N,N,N'-trimethylurea,
N,N'-dimethyl-N-ethylurea,
N,N-dimethyl-N'-i-propylurea,
N,N-diethyl-N'-methylurea,
N,N,N'-triethylurea,
N-ethyl-N-n-propyl-N'-methylurea, etc.

The process of this invention may be effected by reacting the starting compound (II) with the urea derivative (III) at a temperature in the range of 0° to 150° C, preferably from 10° to 90° C, in an inert solvent. The inert solvent includes, illustratively, a lower alkanol (e.g. methanol, ethanol, i-propanol), lower halogenoalkane (e.g. methylene chloride, chloroform, carbon tetrachloride, ethylene chloride), aromatic hydrocarbon (e.g. benzene, toluene, xylenes), aliphatic hydrocarbon (e.g. n-hexane, petroleum benzin, cyclohexane), aromatic tertiary base (e.g. pyridine, picoline, collidine), dimethylformamide, dimethylsulfoxide, and hexamethylenephosphamide. For accelerating the condensation, there may be optionally incorporated any suitable additive, i.e. alkali-metal alcoholate (e.g. sodium methoxide, potassium ethoxide), aliphatic tertiary amine (e.g. triethylamine), aromatic tertiary base (e.g pyridine, lutidine), and alkaline salt (e.g. sodium bicarbonate, lithium acetate, calcium carbonate). The reaction can be executed substantially in a conventional manner as in a usual formation process of a carbonyl ureide. The condensation reaction takes place readily to give the objective 3-isoxazolylcarbonylureide derivatives (I) in a high yield.

The said 3-isoxazolylcarbonylureide derivatives (I) include, illustratively:

N-(3-isoxazolylcarbonyl)urea,
N-(3-isoxazolylcarbonyl)thiourea,
1-(3-isoxazolylcarbonyl)guanidine,
N-(5-methyl-3-isoxazolylcarbonyl)urea,
N-(5-ethyl-3-isoxazolylcarbonyl)urea,
N-(5-n-propyl-3-isoxazolylcarbonyl)urea,
N-(5-i-propyl-3-isoxazolycarbonyl)urea,
N-(5-t-butyl-3-isoxazolylcarbonyl)urea,
N-5-cyclopropyl-3-isoxazolylcarbonyl)urea,
N-(5-methyl-3-isoxazolylcarbonyl)thiourea,
1-(5-methyl-3-isoxazolylcarbonyl)guanidine,
N-methyl-N-(3-isoxazolylcarbonyl)urea,
N-methyl-N-(5-methyl-3-isoxazolylcarbonyl)urea,
N-ethyl-N-(5-methyl-3-isoxazolylcarbonyl)urea,
N-i-propyl-N-(5-methyl-3-isoxazolylcarbonyl)urea,
N-methyl-N-(5-ethyl-3-isoxazolylcarbonyl)urea,
N-n-propyl-N-(5-ethyl-3-isoxazolylcarbonyl)urea,
N'-methyl-N-(5-methyl-3-isoxazolylcarbonyl)urea,
N'-ethyl-N-(5-methyl-3-isoxazolylcarbonyl)urea,
N'-n-propyl-N-(5-methyl-3-isoxazolylcarbonyl)urea,
N'-i-propyl-N-(5-methyl-3-isoxazolylcarbonyl)urea,
N'-n-butyl-N-(5-methyl-3-isoxazolylcarbonyl)urea,
N'-s-butyl-N-(5-methyl-3-isoxazolylcarbonyl)urea,
N'-i-propyl-N-(5-ethyl-3-isoxazolylcarbonyl)urea,
N'-i-propyl-N-(5-n-propyl-3-isoxazolylcarbonyl)urea,
N'-i-propyl-N-(5-i-propyl-3-isoxazolylcarbonyl)urea,
N'-i-propyl-N-(5-t-butyl-3-isoxazolylcarbonyl)urea,
N'-i-propyl-N-(5-cyclopropyl-3-isoxazolylcarbonyl)urea,
N'-cyclohexyl-N-(5-methyl-3-isoxazolylcarbonyl)urea,
N'-(1-adamantyl)-N-(5-methyl-3-isoxazolylcarbonyl)urea,
N'-phenyl-N-(5-methyl-3-isoxazolylcarbonyl)urea,
N,N'-dimethyl-N-(5-methyl-3-isoxazolylcarbonyl)urea,
N,N'-diethyl-N-(5-methyl-3-isoxazolylcarbonyl)urea,
N,N'-dicyclohexyl-N-(5-methyl-3-isoxazolylcarbonyl)urea,
N,N'-dicyclohexyl-N-(5-ethyl-3-isoxazolylcarbonyl)urea,
N,N'-dicyclohexyl-N-(5-cyclopropyl-3-isoxazolylcarbonyl)urea,
N,N'-dicyclohexyl-N-(5-t-butyl-3-isoxazolylcarbonyl)urea,
N-methyl-N'-ethyl-N-(5-methyl-3-isoxazolylcarbonyl)urea,
N-ethyl-N'-methyl-N-(5-methyl-3-isoxazolylcarbonyl)urea,
N,N'-di-i-propyl-N-(5-ethyl-3-isoxazolylcarbonyl)urea,
N',N'-dimethyl-N-(3-isoxazolylcarbonyl)urea,
N',N'-dimethyl-N-(5-methyl-3-isoxazolylcarbonyl)urea,
N',N'-dimethyl-N-(5-ethyl-3-isoxazolylcarbonyl)urea,
N',N'-dimethyl-N-(5-cyclopropyl-3-isoxazolylcarbonyl)urea,
N',N'-diethyl-N-(5-methyl-3-isoxazolylcarbonyl)urea,
N',N'-diethyl-N-(5-ethyl-3-isoxazolylcarbonyl)urea,
N'-methyl-N'-ethyl-N-(5-methyl-3-isoxazolylcarbonyl)urea,
N'-i-propyl-N'-n-propyl-N-(5-methyl-3-isoxazolylcarbonyl)urea,
4-[(5-methyl-3-isoxazolyl)carbonylaminocarbonyl]-morpholine,
N,N',N'-trimethyl-N-(5-methyl-3-isoxazolylcarbonyl)urea,
N-ethyl-N',N'-dimethyl-N-(5-methyl-3-isoxazolylcarbonyl)urea,
N-i-propyl-N',N'-dimethyl-N-(5-ethyl-3-isoxazolylcarbonyl)urea,
N-methyl-N',N'-diethyl-N-(5-methyl-3-isoxazolylcarbonyl)urea,
N,N',N'-triethyl-N-(5-methyl-3-isoxazolylcarbonyl)urea,
N-methyl-N'-ethyl-N'-n-propyl-N-(5-ethyl-3-isoxazolylcarbonyl)urea, and
N-n-propyl-N',N'-diethyl-N-(5-ethyl-3-isoxazolylcarbonyl)urea.

These 3-isoxazolylcarbonylureide derivatives (I) are novel compounds and are available as potent antidiabetics, showing a superior hypoglycemic or blood-sugar regulating effect to that of known synthetic drugs (e.g. sulfonylureas, biguanides, mesoxalate), normalizing the level of blood free-fatty-acid (BFFA) concentration, and lowering the cholesterol-level in the mammalian blood stream, when administered orally or parenterally to more or less diabetic mammals. Since some known hypoglycemic substances in the isoxazole series (i.e. 5-isoxazolylcarbonylureides of Japanese Pat. No. 575,312) cause within a short time a kind of drug-tolerance in tested living-bodies and their desired pharmacodynamic activity rapidly diminishes, even within an administration period of 2 or 3 days, they cannot be used in practice as positive and durable antidiabetics. It is one of the excellent advantages of the present invention that the objective 3-isoxazolylcarbonylureide derivatives (I) bring about no drug-tolerance except to their relatively low toxicity. Further, the isoxazole compounds (I) are available as a new type of much safer and more potent antidiabetic, particularly suitable for long-term treatment of various types of human diabetes, and they have no serious side-actions either in diabetic patients or on a normal control.

Biological activity of some isoxazole derivatives (I) is determined by the following assay experiment in comparison with the known sulfonylurea antidiabetic, tolbutamide.

ASSAY EXPERIMENT (1) Hypoglycemic Activity:

a) Test Compound

| Compound No. | Chemical Name |
| --- | --- |
| 1 | N'-i-propyl-N-(5-ethyl-3-isoxazolylcarbonyl)-urea |
| 2 | N',N'-dimethyl-N-(5-methyl-3-isoxazolylcarbonyl)-urea |
| 3 | 1-(5-methyl-3-isoxazolylcarbonyl)guanidine |
| 4 | N,N'-dimethyl-N-(5-methyl-3-isoxazolylcarbonyl)-urea |
| 5 | N,N',N'-trimethyl-N-(5-methyl-3-isoxazolylcarbonyl)urea |
| 6 | Tolbutamide (a known drug, for comparison | b) Test Method

Assay and control groups of rats were used, each group consisting of 5 adult male rats weighing 200 to 250 g and showing about 250 to 350 mg/dl-blood as the initial blood-sugar value, after being treated once with 50 mg/kg of alloxan (i.v.) one week before the assay. The assay and control groups were orally administered a 5 % gum arabic suspension with and without the test compound, respectively. Measurement of the absolute blood-sugar value was carried out thrice (i.e. 1 hour after, 3 hours after, and 5 hours after administration) and the values were compared with those of the control group. Blood-sugar values were determined by an assay technique using the marketed enzymatic glucose reagent: Glucostat (Trade Mark of Worthington Biochemical Corporation, Freehold, N.J., U.S.A.). Results on the hypoglycemic activity of compounds 1 to 6 are shown by a special percentage factor of the Blood-Sugar-Level (B.S.L.) which can be calculated from the following equation:

$$B.S.L. = \frac{\left[\begin{array}{c}\text{B.S. mean value} \\ \text{in assay group}\end{array}\right] - \left[\begin{array}{c}\text{B.S. mean value} \\ \text{in control group}\end{array}\right]}{[\text{B.S. mean value in control group}]} \times 100\ (\%)$$

Table I shows the calculated B.S.L. data together with total of the three percentages actually determined for each compound.

c) Result

Table I

| Test Compound No. | 100 mg/kg dose | | | | 10 mg/kg Dose | | | |
| --- | --- | --- | --- | --- | --- | --- | --- | --- |
| | 1 hr after | 3 hr after | 5 hr after | Total | 1 hr after | 3 hr after | 5 hr after | Total |
| 1 | −54 | −63 | −43 | −160 | −8 | +2 | +2 | −4 |
| 2 | −33 | −59 | −59 | −151 | −45 | −59 | −29 | −133 |
| 3 | −30 | −56 | −52 | −138 | −11 | −39 | −32 | −82 |
| 4 | −22 | −51 | −59 | −132 | −15 | −36 | −20 | −71 |
| 5 | −24 | −40 | −40 | −104 | −19 | −39 | −39 | −97 |
| 6 | −9 | −26 | −23 | −58 | — | — | — | — |

In effect, the marks + and − correspond to increasing and decreasing tendency of B.S.L., respectively, after eliminating the difference in value between the assay and control groups.

(2) Blood Free-Fatty-Acid (B.F.F.A.) Lowering Activity a) Test Method

Several groups of male rats weighing 200 to 250 g, each group consisting of 5 rats, were used in the test. Assay and control groups were fasted during 24 hours and then orally given 5 % gum arabic suspension with and without the test compound (100 mg/kg p.o.), respectively. All animals tested were decapitated 1 hour after, 3 hours after, or 5 hours after the treatment, and blood samples were drawn for B.F.F.A. value determination. A percentage factor, as B.F.F.A. Level, was determined according to the Itaya-Ui method [K. Itaya, et al.: J. Lipid Research, Vol. 6, 18 (1965)], calculated by the following equation:

$$B.F.F.A.\ \text{Level} = \frac{\left[\begin{array}{c}\text{B.F.F.A. mean value} \\ \text{in assay group}\end{array}\right] - \left[\begin{array}{c}\text{B.F.F.A. Mean Value} \\ \text{in control group}\end{array}\right]}{[\text{B.F.F.A. Mean Value in control group}]} \times 100\ (\%)$$

b) Result

B.F.F.A. Levels are shown in Table II, together with + and − marks and the total of the three values for each compound.

Table II.

B.F.F.A. Level after Treatment with Test Compounds.

| Test Compound (100 mg/kg p.o.) | B.F.F.A. Level (%) | | | |
| --- | --- | --- | --- | --- |
| | 1 hr after | 3 hr after | 5 hr after | Total |
| N'-n-butyl-N-(5-methyl-3-isoxazolylcarbonyl urea | −59 | −59 | −30 | −129 |
| N'-i-propyl-N-(5-methyl-3-isoxazolylcarbonyl)urea | −75 | −67 | −49 | −191 |
| N'-cyclohexyl-N-(5-methyl-3-isoxazolylcarbonyl)urea | −27 | −34 | −23 | −84 |
| 1-(5-methyl-3-isoxazolylcarbonyl)guanidine | −70 | −15 | −8 | −93 |
| N-(5-methyl-3-isoxazolylcarbonyl)thiourea | −60 | −36 | +13 | −83 |
| Tolbutamide | −40 | −45 | 0 | −85 |

(3) Acute Toxicity a) Test Method

The 50 % lethal dose ($LD_{50}$) was determined as follows: Test compounds were given orally to DS-strain albino mice at various single doses. For each dose 10 male mice were used, their body-weights ranging from 19 to 21 grams. The test animals were observed for 24 hours after administration of the test compound. The $LD_{50}$ means the amount of the test compound being expected to kill just half the number of the animals treated. This was calculated by graphic interpolation from two doses actually used, one of which killed less than half, and the other more than half the number of mice treated (Schleicher — Schull's probability graphic paper 298 ½ was used for the graphic interpolation).

b) Result

Results of the acute toxicity test are shown in Table III.

Table III.

| Acute Toxicity of Test Compounds | |
|---|---|
| Compound | $LD_{50}$ (g/kg) |
| N'-i-propyl-N-(5-methyl-3-isoxazolyl-carbonyl)urea | 7.0 – 8.0 |
| N-(5-methyl-3-isoxazolylcarbonyl)-urea | over 10.0 |
| 1-(5-methylisoxazolylcarbonyl-guanidine | 2.0 – 3.0 |
| Tolbutamide | 1.7 – 1.9 |

(4) Evaluation

It can be said that some compounds (I) of the present invention show much more powerful hypoglycemic activity and much less toxicity than those of the well-known sulfonylurea antidiabetic, tolbutamide.

The said isoxazole products (I) can be administered alone or in combination with acceptable pharmaceutical carriers, the choice of which depends on the preferred route of administration, solubility of the materials, and pharmaceutical practice. In general, the dosage of these products (I) is on the order of the same to one tenth of the practical dosage of tolbutamide. The products (I) are useful for treating various types of mammalian diabetes, with or without the commercially known hypoglycemic agents. Practical examples of pharmaceutical preparations with the products (I) are tablets, capsules, pills, suspension, emulsion, solution, suppositories, granules, and powder. In the preparation of tablets, for example, these products (I) can be combined with binders such as gum tragacanth, acacia, corn starch, gelatin, etc. It is also usually desirable to have a disintegrating agent or diluent such as corn starch, potato starch, wheat starch, alginic acid or the like. Also preferably available is a lubricant such as stearic acid, magnesium stearate or talc along with a sweetening agent such as saccharin. Flavoring agents may be also used, such as peppermint, wintergreen oil or cherry flavor. In the preparation of capsules, adjuvants such as enumerated above for tablets can also be available. The composition when used in the form of suspension or solution may be combined with syrup or sorbitol type vehicle including a viscosity controller such as magnesium aluminum silicate, methocel, or carboxymethylcellulose, and a suitable preservative such as sodium benzoate, methyl or propyl paraben. In these liquid preparations, colorings, flavorings, and bufferings may also be included to produce a pharmaceutically more elegant preparation.

The compositions containing the isoxazole derivatives (I) can be dispensed in dosage unit forms for a single daily therapeutic dose, in smaller units for multiple doses, or in larger units for dividing into single doses. Parenteral compositions can also be prescribed in single units or in larger quantities from which each single dosage will be withdrawn before use.

Presently preferred and practical embodiments of the present invention are illustrated shown by the following examples. In these examples, the relationship of parts-by-weight to parts-by-volume has the same meaning as that between grams and milliliters. Temperatures are given in degrees centigrade.

EXAMPLE 1

To a suspension of 5-methylisoxazole-3-carboxylic acid (130 parts by weight) in benzene (1,000 parts by volume), thionyl chloride (150 parts by weight) and pyridine (10 parts by volume) are added under stirring while keeping the reaction temperature below 20° C. The resultant mixture is heated gradually and refluxed for 3 hours. The reaction mixture is evaporated to dryness under reduced pressure to remove the solvent and the remaining reagent, and then the residue is treated with cold benzene (500 parts by volume) and filtered.

To the solution of 5-methyl-3-isoxazolylcarbonyl chloride in benzene thus obtained, a solution of N-i-propylurea (85 parts by weight) is added dropwise within an hour under stirring and ice-cooling. The resultant mixture is allowed to stand at 20° C for 12 hours, heated at 50° C and then evaporated to dryness under reduced pressure. The remaining residue is washed with cold distilled water (1,000 parts by volume) to give a crude product as N'-i-propyl-N-(5-methyl-3-isoxazolylcarbonyl)urea (110 parts by weight). The crude product is recrystallized from a mixture of methylene chloride and benzene to give colorless needles melting at 164° to 165° C. IR (Nujol):3315,3280, 1685 – 1697 $cm^{-1}$ (major absorptions).

EXAMPLE 2

When the reaction is effected as in Example 1 except that N-n-butylurea is used in lieu of N-i-propylurea, N'-n-butyl-N-(5-methyl-3-isoxazolylcarbonyl)urea is obtained as colorless prisms melting at 139° to 140° C. IR (Nujol): 1696 $cm^{-1}$ (=C=O).

EXAMPLE 3

When the reaction is effected as in Example 1 except that N-cyclohexylurea is used instead of N-i-propylurea, N'-cyclohexyl-N-(5-methylisoxazolylcarbonyl)urea is obtained as colorless plates melting at 180° to 180.5° C (recrystallized from methanol). IR (Nujol): 1690 $cm^{-1}$ (=C=O).

EXAMPLE 4

To a solution of sodium ethylate (75 parts by weight) in anhydrous ethanol (500 parts by volume), guanidine monohydrochloride (96 parts by weight) is added under stirring and ice-cooling to make an ethanolic solution of free guanidine. To this solution, a solution of ethyl 5-methylisoxazole-3-carboxylate (155 parts by weight) in anhydrous ethanol (200 parts by volume) is added within 2 hours under stirring at 40° C. The resultant mixture is allowed to stand at 20° C for 12 hours. The precipitated crude crystals are filtered off, washed with a small amount of water and recrystallized from ethanol to give 1-(5-methyl-3-isoxazolylcarbonyl)-guanidine as colorless prisms melting at 192° to 192.5° C under decomposition. IR (Nujol): 1652 cm$^{-1}$ (=C=O).

EXAMPLE 5

When the reaction is effected as in Example 1 except that free urea is used in lieu of i-propylurea in the medium of toluene at 80°–110° C, N-(5-methyl-3-isoxazolylcarbonyl)urea is obtained as colorless needles melting at 238.5° C (decomp.). IR (Nujol): 1701, 1663 cm$^{-1}$ (=C=O).

EXAMPLE 6

When the reaction is effected as in Example 5 except that thiourea is used in place of urea, N-(5-methyl-3-isoxazolylcarbonyl)thiourea is obtained as colorless needles melting at 218° to 218.5° C (decomp.). IR (Nujol): 1699, 1610 cm$^{-1}$ (=C=O).

EXAMPLE 7 – 37

These reactions are effected as in Example 5, and the corresponding ureide derivatives (I) are obtained as shown in Table IV.

EXAMPLE 38

The following materials are admixed and micropulverized in a pharmaceutical manner:

| | |
|---|---|
| N-(5-methyl-3-isoxazolylcarbonyl)urea | 50.0 g |
| Lactose | 97.0 g |
| Wheat starch | 49.0 g |

The composition thus formed is kneaded with 5% aqueous potato starch paste (40.0 g) and granulated with a granulator. The granules are dried in an oven at 50° C, sieved through a 16 mesh screen, lubricated with magnesium stearate (2.0 g) and compressed into tablets each weighing 200 mg in 8 mm deep concave punches to give just 1,000 tablets. Each tablet contains 50 mg of the active ingredient as N-(5-methyl-3-isoxazolylcarbonyl)urea.

EXAMPLE 39

N',N'-Dimethyl-N-(5-methyl-3-isoxazolylcarbonyl)urea (125 g) is dissolved into physiological saline solution to give 10 liter volume and filtered. The resultant solution is divided and filled into 5,000 ampoules under nitrogen atmosphere, and all ampoules are sterilized in an autoclave at 115° C for 30 minutes. Each ampoule (net volume: 2 milliliters) contains 25 mg of the active ingredient as N',N'-dimethyl-N-(5-methyl-3-isoxazolylcarbonyl)urea.

Table IV.

| | | | 31 Products as Ureides*) | | | | |
|---|---|---|---|---|---|---|---|
| Ex. | II | | III | | | Property of the Product (I) | |
| NO. | R$^1$ | X | R$^2$ | R$^3$ | R$^4$ | Y | m.p. (° C) | IR: cm$^{-1}$ (Medium) |
| 7 | Et | Br | H | i-Pr | H | O | 137.0–138.5 | 1725, 1700 (CCl$_4$) |
| 8 | n-Pr | Cl | H | i-Pr | H | O | 133.5–135.0 | 1726, 1702 (CCl$_4$) |
| 9 | i-Pr | Cl | H | i-Pr | H | O | 95.5–96.5 | 1727, 1701 (CCl$_4$) |
| 10 | t-Bu | Cl | H | i-Pr | H | O | 104–105 | 1726, 1700 (CCl$_4$) |
| 11 | C-Pr | Cl | H | i-Pr | H | O | 126–127 | 1724, 1701 (CCl$_4$) |
| 12 | Et | Br | H | H | H | O | 220.0–220.5 | 1690 (Nujol) |
| 13 | n-Pr | Cl | H | H | H | O | 210–213 | 1695 (Nujol) |
| 14 | t-Bu | Cl | H | H | H | O | 186–188 | 1693 (Nujol) |
| 15 | C-Pr | Cl | H | H | H | O | 226–227 | 1669 (Nujol) |
| 16 | i-Pr | Cl | H | H | H | O | 205.0–205.5 | 1695 (Nujol) |
| 17 | Me | Cl | H | Me | H | O | 212–213 | 1690 (Nujol) |
| 18 | Me | Cl | H | Et | H | O | 160–162 | 1683–1690 (Nujol) |
| 19 | Me | Cl | H | n-Pr | H | O | 150.5–151.5 | 1694 (Nujol) |
| 20 | Me | Cl | H | s-Bu | H | O | 149–150 | 1687 (Nujol) |
| 21 | Me | Cl | H | 1-Ad | H | O | 191–192 | 1692 (Nujol) |
| 22 | Me | Cl | H | Ph | H | O | 197 | 1706, 1688 (Nujol) |
| 23 | Me | Cl | H | Me | Me | O | 84–85 | 1684 (Nujol) |
| 24 | Me | Cl | H | CH$_2$CH$_2$–O–CH$_2$CH$_2$ | | O | 105.5–106.5 | 1697–1707 (Nujol) |
| 25 | Me | Cl | Me | Me | H | O | 57–58 | 1647 (Nujol) |
| 26 | Me | Cl | Me | Me | Me | O | 93.5–95 | 1686, 1671 (Nujol) |
| 27 | H | I | H | H | H | O | 217.5–218.5 | 1975, 1619 (CHCl$_3$) |
| 28 | Me | Cl | H | Et | Et | O | 65.5–66.5 | 1748, 1682 (CHCl$_3$) |
| 29 | Me | Cl | C-He | C-He | H | O | 151.5–152.0 | 1701, 1660 (Nujol) |
| 30 | Et | Cl | C-He | C-He | H | O | 133.0–134.0 | 1712, 1658 (CCl$_4$) |
| 31 | C-Pr | Cl | C-He | C-He | H | O | 143.0–144.0 | 1712, 1661 (CCl$_4$) |
| 32 | t-Bu | Cl | C-He | C-He | H | O | 158.5–159.0 | 1707, 1660 (CHCl$_3$) |
| 33 | H | Cl | H | Me | Me | O | 107.5–108.5 | 1750, 1719, 1689 (CHCl$_3$) |
| 34 | Me | Cl | H | Me | Et | O | Colorless oil | 1750, 1716, 1685 (CHCl$_3$) |
| 35 | Et | Cl | H | Me | Me | O | Colorless oil | 1749, 1689 (CHCl$_3$) |
| 36 | Et | Cl | H | Et | Et | O | Oil | 1747, 1717, 1680 |
| 37 | C-Pr | Cl | H | Me | Me | O | 57.0–58.5 | 1749, 1689 (CHCl$_3$) |

*) The abbreviations in Table IV are as following: Ex. No. (example number), m.p. (melting point), IR (infrared maximum absorption), Me (methyl), Et (ethyl), i-Pr (isopropyl), t-Bu (tertiary butyl), C- (cyclo-), n- (normal-), s-(secondary-), 1-Ad (1-adamantyl, Ph (phenyl), and He (hexyl).

What is claimed is:
1. A compound of the formula

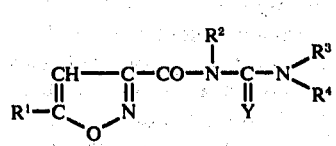

wherein each of $R^1$ and $R^2$ is hydrogen, alkyl of 1 to 8 carbon atoms or cycloalkyl of 3 to 10 carbon atoms, each of $R^3$ and $R^4$ is hydrogen, alkyl of 1 to 8 carbon atoms, cycloalkyl of 3 to 10 carbon atoms or phenyl, or the group

is morpholino, and Y is oxo.

2. A compound according to claim 1, wherein $R^3$ and $R^4$ are each hydrogen, alkyl of 1 to 8 carbon atoms, cycloalkyl of 3 to 10 carbon atoms or phenyl.

3. A compound according to claim 1 represented by the formula

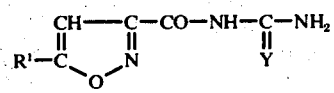

wherein $R^1$ is hydrogen, alkyl of 1 to 8 carbon atoms or cycloalkyl of 3 to 10 carbon atoms, and Y is oxo.

4. The compound according to claim 3, namely N-(5-methyl-3-isoxazolylcarbonyl)urea.

5. The compound according to claim 3, namely N-(5-ethyl-3-isoxazolylcarbonyl)urea.

6. The compound according to claim 3, namely N-(5-n-propyl-3-isoxazolylcarbonyl)urea.

7. The compound according to claim 3, namely N-(5-cyclopropyl-3-isoxazolylcarbonyl)urea.

8. The compound according to claim 3, namely N-(5-t-butyl-3-isoxazolylcarbonyl)urea.

9. The compound according to claim 3, namely N-(5-i-propyl-3-isoxazolylcarbonyl)urea.

10. The compound according to claim 3, namely N-(3-isoxazolylcarbonyl)urea.

11. A compound according to claim 1 represented by the formula

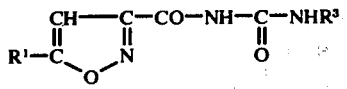

wherein $R^1$ is hydrogen, alkyl of 1 to 8 carbon atoms or cycloalkyl of 3 to 10 carbon atoms, and $R^3$ is alkyl of 1 to 8 carbon atoms, cycloalkyl of 3 to 10 carbon atoms or phenyl.

12. The compound according to claim 11, namely N'-i-propyl-N-(5-methyl-3-isoxazolylcarbonyl)urea.

13. The compound according to claim 11, namely N'-n-butyl-N-(5-methyl-3-isoxazolylcarbonyl)urea.

14. The compound according to claim 11, namely N'-cyclohexyl-N-(5-methyl-3-isoxazolylcarbonyl)urea.

15. The compound according to claim 11, namely N'-i-propyl-N-(5-ethyl-3-isoxazolylcarbonyl)urea.

16. The compound according to claim 11, namely N'-i-propyl-N-(5-n-propyl-3-isoxazolylcarbonyl)urea.

17. The compound according to claim 11, namely N'-i-propyl-N-(5-i-propyl-3-isoxazolylcarbonyl)urea.

18. The compound according to claim 11, namely N'-i-propyl-N-(5-t-butyl-3-isoxazolylcarbonyl)urea.

19. The compound according to claim 11, namely N'-i-propyl-N-(5-cyclopropyl-3-isoxazolylcarbonyl)urea.

20. The compound according to claim 11, namely N'-methyl-N-(5-methyl-3-isoxazolylcarbonyl)urea.

21. The compound according to claim 11, namely N'-ethyl-N-(5-methyl-3-isoxazolylcarbonyl)urea.

22. The compound according to claim 11, namely N'-n-propyl-N-(5-methyl-3-isoxazolylcarbonyl)urea.

23. The compound according to claim 11, namely N'-s-butyl-N-(5-methyl-3-isoxazolylcarbonyl)urea.

24. The compound according to claim 11, namely N'-1-adamantyl-N-(5-methyl-3-isoxazolylcarbonyl)urea.

25. The compound according to claim 11, namely N'-phenyl-N-(5-methyl-3-isoxazolylcarbonyl)urea.

26. A compound according to claim 1 represented by the formula

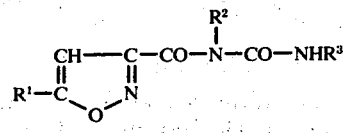

wherein $R^1$ is alkyl of 1 to 8 carbon atoms, and $R^2$ and $R^3$ are each alkyl of 1 to 8 carbon atoms or cycloalkyl of 3 to 10 carbon atoms.

27. A compound according to claim 26, namely N,N'-dimethyl-N-(5-methyl-3-isoxazolylcarbonyl)urea.

28. A compound according to claim 1 represented by the formula

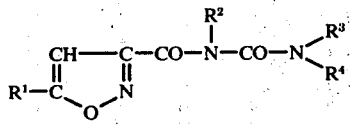

wherein $R^1$ is alkyl of 1 to 8 carbon atoms or cycloalkyl of 3 to 10 carbon atoms, $R^2$ is hydrogen or alkyl of 1 to 8 carbon atoms, and $R^3$ and $R^4$ are each alkyl of 1 to 8 carbon atoms, or the group

is morpholino.

29. The compound according to claim 28, namely N',N'-dimethyl-N-(5-methyl-3-isoxazolylcarbonyl)urea.

30. The compound according to claim 28, namely 4-[(5-methyl-3-isoxazolyl)carbonylaminocarbonyl]-morpholine.

31. The compound according to claim 28, namely N,N',N'-trimethyl-N-(5-methyl-3-isoxazolylcarbonyl)urea.

32. The compound according to claim 28, namely N',N'-diethyl-N-(5-methyl-3-isoxazolylcarbonyl)urea.

33. The compound according to claim 28, namely N'-i-propyl-N'-n-propyl-N-(5-methyl-3-isoxazolylcarbonyl)urea.

34. The compound according to claim 28, namely N'-methyl, N'-ethyl-N-(5-methyl-3-isoxazolylcarbonyl)urea.

* * * * *